(12) United States Patent
Brown

(10) Patent No.: US 7,304,047 B2
(45) Date of Patent: Dec. 4, 2007

(54) METHOD OF TREATING SUBSTANCE ABUSE WITH QUETIAPINE

(75) Inventor: Sherwood Brown, Dallas, TX (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/470,368

(22) PCT Filed: Feb. 5, 2002

(86) PCT No.: PCT/SE02/00214

§ 371 (c)(1),
(2), (4) Date: Jul. 25, 2003

(87) PCT Pub. No.: WO02/062346

PCT Pub. Date: Aug. 15, 2002

(65) Prior Publication Data

US 2004/0058910 A1     Mar. 25, 2004

Related U.S. Application Data

(60) Provisional application No. 60/266,808, filed on Feb. 6, 2001.

(51) Int. Cl.
*A61K 31/553* (2006.01)

(52) U.S. Cl. .................................. 514/211.13

(58) Field of Classification Search ............... 514/219, 514/211.13

See application file for complete search history.

(56) References Cited

U.S. PATENT DOCUMENTS

| 4,879,288 A | 11/1989 | Warawa et al. |
| 6,147,072 A * | 11/2000 | Bymaster et al. ........... 514/220 |

FOREIGN PATENT DOCUMENTS

| WO | WO 9843646 | 10/1998 |
| WO | WO 0071106 | 11/2000 |

OTHER PUBLICATIONS

Sharma et al. Effective treatment of schizophrenia with quetiapine in a 34-year-old caucasian man. International Journal of Psychiatry in Clinical Practice, Mar. 3, 1999 pp. 205-207.*
Product news: Atypical antipsychotics may enhance smoking cessation. INPHARMA Nov. 23, 2000.*
Peter F. Buckley: "Substance Abuse in Schizophrenia: A Review", pp. 26-30, the abstract, p. 28, rt column, J. Clin Psychiatry, vol. 59, suppl. 3, 1998.
International Search Report, Apr. 6, 2003.

* cited by examiner

*Primary Examiner*—Jennifer Kim
(74) *Attorney, Agent, or Firm*—Karen Cochran

(57) ABSTRACT

This invention relates to a method of treating Substance Use such as Substance Abuse or Substance Dependence and in particular to the use of quetiapine in treating such disorders.

1 Claim, No Drawings

METHOD OF TREATING SUBSTANCE ABUSE WITH QUETIAPINE

This application is a U.S. National Phase Application of PCT International Application No. PCT/SE02/00214 which was filed on Feb. 5, 2002 and which claims priority from U.S. application Ser. No. 60/266,808 filed Feb. 6, 2001.

This invention relates to a method of treating Substance Use such as Substance Abuse or Substance Dependence and in particular to the use of quetiapine in treating such disorders.

Patients who suffer from Substance Abuse are those who repeatedly misuse substances such as drugs (including tobacco) and alcohol, usually with significant, adverse consequences. These adverse consequences can include physical incidents (eg driving or operating machinery whilst intoxicated), legal issues (drunk and/or disorderly) and in particular health (physical and mental), social and interpersonal issues (absence from work, disruptive behaviour, neglect of family and colleagues) and related manifestations.

Patients who suffer from Substance Dependence are those who continually use substances such as drugs and alcohol, usually by self-administration. Such patients generally develop a tolerance for these substances with the consequence that increased intake of substance is necessary to achieve the same effect. Another adverse consequence is that such patients may also develop withdrawal symptoms if they attempt to lower their intake of substance. Withdrawal symptoms are unpleasant, damaging and hazardous, and in many, many cases, their occurrence is quite likely to lead to renewed intake of the substance. Further adverse consequences of Substance Dependence are those associated with compulsive use and the social and interpersonal issues that can result from such use.

Quetiapine is an a typical antipsychotic agent which has good efficacy and tolerability and which is useful in the treatment of schizophrenia.

We now believe that quetiapine is useful in treating Substance Use such as Substance Abuse or Substance Dependence and related disorders.

According to the present invention, we provide a method for treating Substance Use or a related disorder which comprises administering an effective amount of quetiapine or a pharmaceutically acceptable salt thereof to a patient in need thereof.

In another aspect, the present invention provides quetiapine or a pharmaceutically acceptable salt thereof for use in treating Substance Use or a related disorder.

In yet a further aspect, the present invention provides the use of quetiapine or a pharmaceutically acceptable salt thereof in the manufacture of a medicament for treating Substance Use or a related disorder.

In a particular aspect, we provide a method for treating Substance Abuse which comprises administering an effective amount of quetiapine or a pharmaceutically acceptable salt thereof to a patient in need thereof.

In another particular aspect, we provide a method for treating Substance Dependence which comprises administering an effective amount of quetiapine or a pharmaceutically acceptable salt thereof to a patient in need thereof.

Substance Use includes Substance Abuse and Substance Dependence and related disorders. In addition to the description above, reference may be made to the definitions in the "Diagnostic and Statistical Manual of Mental Disorders", Fourth Edition published by the American Psychiatric Association, Washington, D.C., USA. This Manual may also be referred to for greater detail on the symptoms and diagnostic features associated with Substance Use, Substance Abuse and Substance Dependence.

Typical substances that lead to Substance Abuse and Substance Dependence include drugs such as amphetamines, cannabis, cocaine, crack, hallucinogenic agents, inhalants, opioids, phencyclidine, sedatives, hypnotics, anxiolytic agents and alcohol. Nicotine can also lead to Substance Dependence.

A particular substance of concern to society is cocaine. Quetiapine has been shown to be beneficial in reducing the cocaine dependence of patients. Quetiapine decreases the craving for the drug; this is particularly useful as it leads to lower drug use (and, ideally, no drug use) with all of the attendant benefits. This may also be described as controlling the patient's impulsivity to take a drug or the patient's drug-seeking behaviour. It can be relatively easy for a patient to return to their drug habits. Patients with a history of drug dependence may be more likely to be hypersensitive to a 'trigger' than the normal person and may be more likely to relapse more easily; for example the end of a meal may be a 'trigger' for a tobacco smoker to light a cigarette or cigar.

Thus, in another aspect, the present invention provides a method of reducing the craving or impulsivity of a patient for a Substance which comprises administering an effective amount of quetiapine or a pharmaceutically acceptable salt thereof to a patient in need thereof. Also, the present invention provides a method of treating withdrawal symptoms in a patient in need thereof, which symptoms result from stopping or lessening of the intake of Substance, which method comprises administering an effective amount of quetiapine or a pharmaceutically acceptable salt thereof.

Quetiapine is 11-(4-[2-(2-hydroxyethoxy)ethyl]-1-piperazinyl)dibenzo[b,f][1.4]-thiazepine. This compound, pharmaceutically acceptable salts thereof and its use in treating schizophrenia are described in granted European Patent No. EP 240,228 and in corresponding patents.

The method of treatment of the present invention may be conducted over a short term (5-6 weeks), medium term (1-6 months) or long term (6 months-2 years or more) treatment, and is particularly valuable in medium term treatment. In a particular aspect, quetiapine does not exhibit the significant weight gain seen with some other a typical antipsychotics. Thus, it is particularly suitable for longer term treatment. In addition, quetiapine lowers the incidence of depression and anxiety and these are very useful benefits from the treatment of patients suffering from Substance Abuse and Substance dependence. Furthermore quetiapine shows minimal extrapyramidal symptoms at typical dosage amounts and exhibits valuable sedative properties.

Quetiapine may be administered as the compound, 11-(4-[2-(2-hydroxyethoxy)ethyl]-1-piperazinyl)-dibenzo[b,f][1.4]thiazepine or may be administered in the form of a pharmaceutically acceptable salt. Examples of suitable salts include, for example, chloride, maleate, fumarate, citrate, phosphate, methane sulphonate and sulphate salts. Preferred salts include fumarates and a particularly preferred salt is the hemi-fumarate.

It is generally preferred that 11-(4-[2-(2-hydroxyethoxy)ethyl]-1-piperazinyl)-dibenzo[b,f][1.4]thiazepine is administered in the form of a pharmaceutically acceptable salt, and in particular a fumarate (2:1) salt.

In the treatment of the conditions mentioned above quetiapine or a pharmaceutically acceptable salt may be administered orally or parenterally in a conventional dosage form such as tablets, pills, capsules, injectables or the like. The dosage in mg/kg of body weight of the compound used to treat patients will vary according to the size of the patient and particularly with respect to the brain/body weight ratio. In general, a higher mg/kg dosage for an adolescent will have the same effect as a lower mg/kg dosage in an adult human. A minimum effective dosage for quetiapine or a pharmaceutically acceptable salt thereof will be about 0.5 mg/kg of body weight per day with a maximum dosage of about 200 mg/kg per day.

A dosage of about 0.5 to 40 mg/kg per day will generally be effective. Typically, a dosage of about 50 mg to 1200 mg per day will generally be effective. Usually, a dosage of about 150 mg to 800 mg per day will be administered, with a convenient dosage being about 500-1000 mg per day. In some groups of patients a lower dosage may be preferred such as 250 mg per day. The dosage can be given once daily or in divided doses, for example, 2 to 4 doses daily. The dose may be conventionally formulated in an oral or parenteral dosage form by compounding 25 to 500 mg per unit dosage of conventional vehicle, excipient, binder, preservative, stabiliser, flavour or the like as called for by accepted pharmaceutical practice, for example, as described in U.S. Pat. No. 3,755,340.

Quetiapine or a pharmaceutically acceptable salt may be used in pharmaceutical compositions as the sole active ingredient or may be contained in a pharmaceutical composition together with one or more other active ingredients, or it may be co-administered with one or more known drugs.

Quetiapine or a pharmaceutically acceptable salt may be administered in conjunction with one or more other agents useful for treating Substance Abuse and Substance Dependence, for example naltrexone, methadone and tricyclic antidepressants.

As indicated above, where quetiapine or a pharmaceutically acceptable salt is administered in conjunction with another agent it maybe administered simultaneously, sequentially or separately with that other agent or agents. Thus, as indicated above, quetiapine or a pharmaceutically acceptable salt may be formulated with the other agent or agents or may be presented as a separate formulation.

Thus, in one aspect of the present invention, there is provided a pharmaceutical composition comprising quetiapine or a pharmaceutically acceptable salt and an agent known for treating Substance Abuse, Substance Dependence or a related disorder together with a pharmaceutically acceptable diluent or carrier.

In a further aspect there is provided a pharmaceutical composition comprising quetiapine or a pharmaceutically acceptable salt and an agent for treating Substance Abuse, Substance Dependence or a related disorder for simultaneous, sequential or separate administration.

The preparation of 11-(4-[2-(2-hydroxyethoxy)ethyl]-1-piperazinyl)-dibenzo[b,f][1.4] thiazepine and its pharmaceutically acceptable salts is described in, for example, granted European Patents Nos. EP 240,218; EP 282,236 and in International Patent Application No. PCT/GB98/02260. This compound is commercially available under the generic name quetiapine fumarate.

The invention will now be illustrated with reference to the following, non-limiting examples in which quetiapine was used as the fumarate (2:1) salt.

EXAMPLE 1

Open-label quetiapine was administered to 12 outpatients with bipolar disorder and cocaine dependence. Each outpatient was given a baseline evaluation, which included a structured clinical interview, Hamilton Depression Scale (HDRS), Young Mania Rating Scale (YMRS), Brief Psychiatric Rating Scale (BPRS), a 10-item version of the cocaine craving questionnaire (CCQ), a urine toxicology screen, and self-report of drug use, including dollar amount spent on drugs during the past week. The patients, consisting of 5 men and 7 women, 10 with bipolar I disorder and 2 with bipolar II disorder, with a mean age of 35.4±8.2 years, returned every 2 weeks for 12 weeks.

The patients received quetiapine in the range 50-100 mg/qhs (at bedtime) and the dose was titrated upwards as indicated for psychiatric symptoms and drug use. The mean maximum quetiapine dose was 312.5±95.6 mg/day.

At each appointment the patients reported drug use during the previous week and provided an urine sample. Differences between baseline and exit for patients finishing at least four weeks of therapy were calculated using Student's t-tests and a last observation carried forward (LOCF) technique. Relationships between mood and drug cravings and drug usage were examined using a Pearson correlation (r) matrix.

From baseline to week 12, HDRS, YMRS and BPRS scores improved significantly ($p<0.003$). Cravings significantly decreased as measured by the CCQ ($p<0.05$). A significant correlation was found between baseline and exit changes scores in HDRS and CCQ ($r=0.61$, $p<0.03$) Percent of positive urine samples and dollar amount spent on drugs did not decrease significantly, except that the 8 subjects who completed all 12 weeks of the study showed an 87% reduction (mean $80.8±105.4 to $10.0±17.7; $p=0.043$) in amount spent on drugs. Two of the dropouts reported increased use at the final visit, accounting for the difference between completers and dropouts. Quetiapine was well tolerated, with no subjects withdrawing because of side effects and improvement in mood and drug cravings were found.

EXAMPLE 2

The following illustrates representative pharmaceutical dosage forms containing the compound 11-(4-[2-(2-hydroxyethoxy)ethyl]-1-piperazinyl)-dibenzo[b,f][1,4] thiazepine fumarate (2:1).

|  | mg/tablet |
|---|---|
| (a) Tablet | |
| Quetiapine fumarate | 50.0 |
| Mannitol, USP | 223.75 |
| Croscarmellose sodium | 6.0 |
| Maize starch | 15.0 |
| Hydroxypropylmethylcellulose (HPMC), | 2.25 |
| Magnesium stearate | 3.0 |
| (b) Capsule | |
| Quetiapine fumarate | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

A preferred formulation is that available commercially as quetiapine fumarate.

The invention claimed is:

1. A method of treating cocaine dependence comprising of administering an effective amount of a composition comprising quetiapine or a pharmaceutically acceptable salt thereof to reduce cocaine cravings in a patient in need of treatment of cocaine dependence, wherein said quetiapine is a sole active agent.

* * * * *